United States Patent [19]
Slager

[11] Patent Number: 5,771,895
[45] Date of Patent: Jun. 30, 1998

[54] CATHETER FOR OBTAINING THREE-DIMENSIONAL RECONSTRUCTION OF A VASCULAR LUMEN AND WALL

[76] Inventor: Cornelis J. Slager, Stadhouderstraat 12, 3319 RM Dordrecht, Netherlands

[21] Appl. No.: 637,318

[22] Filed: Apr. 24, 1996

Related U.S. Application Data

[63] Continuation-in-part of Ser. No. 600,140, Feb. 12, 1996.
[51] Int. Cl.⁶ ................................................... A61B 8/00
[52] U.S. Cl. ......................... 128/662.06; 128/660.01; 128/916
[58] Field of Search ................... 128/660.03, 662.06, 128/653.1, 772

[56] References Cited

U.S. PATENT DOCUMENTS

| 4,838,879 | 6/1989 | Tanabe et al. . | |
| 5,054,449 | 10/1991 | Scribner et al. | 128/662.06 |
| 5,063,935 | 11/1991 | Garnbale et al. . | |
| 5,095,911 | 3/1992 | Pomeronz | 128/662.06 |
| 5,255,681 | 10/1993 | Ishimura et al. . | |
| 5,345,938 | 9/1994 | Nishiki et al. . | |
| 5,353,798 | 10/1994 | Sieben . | |
| 5,479,938 | 1/1996 | Weier | 128/772 |
| 5,596,990 | 1/1997 | Yoch et al. | 128/662.06 |

OTHER PUBLICATIONS

Cornelis J. Slager, Martin Laban, Clemens von Birgelen, Rob Krams, Jan A.F. Oomen, Ad den Boer, Li Wenguang, Pim J. de Feyter, Patrick W. Serruys, Jos R.T.C. Roelandt,, "Angus: A New Approach to Three–dimensional Reconstruction of Geometry and Orientation of Coronary Lumen and Plaque by Combined Use of Coronary Angiography and IVUS", *Special Issue Journal of the American College of Cardiology* 44th Annual Scientific Session (Feb. 1995): 144A: 734–6, Abstract.

Cornelis J. Slager, Martin Laban, Jan A.F. Oomen, Clemens von Birgelen, Li Wenguang, Rob Krams, Johan C.H. Schuurbiers, Ad den Boer, Patrick W. Serruys, Jos R.T.C. Roelandt, Pim J. de Feyter, "Three–dimensional geometry and orientation of coronary lumen and plague", *The Thoraxcentre Journal* (1995): 7/3: 36–37.

Jos R.T.C. Roelandt, MD, PhD; Carlo di Mario, MD, PhD: Natesa G. Pandian, MD; Li Wenguang, MSc; David Keane, MB, MRCPI; Cornelis J. Slager, PhD; Pim J. de Feyter, MD, PhD; Patrick W. Serruys, MD, PhD, "Three–dimensional Reconstruction of Intracoronary Ultrasound Images; Rationale, Approaches, Problems, and Directions", *Circulation* (1994) 90: 1044–1055.

James L. Evans, MD; Kok–Hwee Ng, MSEE; Stephen G. Wiet, MD; Michael J. Vonesh, MSEE; William B. Burns, MD; Martin G. Radvany, MD; Bonnie J. Kane, BS; Charles J. Davidson, MD; Sanford I. Roth, MD; Barry L. Kramer, MD; Sheridan N. Meyers, MD; David D. McPherson, MD, "Accurate Three–Dimensional Reconstruction of Intravascular Ultrasound Data; Spatially Correct Three–Dimensional Reconstructions", *Circulation* (1996) 93: 567–576.

(List continued on next page.)

Primary Examiner—Francis Jaworski
Attorney, Agent, or Firm—Lyon & Lyon LLP

[57] ABSTRACT

A catheter system and method of use thereof to obtain accurate three-dimensional reconstruction of a body vessel. The method employs X-ray angiography (ANG) in combination with intravascular ultrasound (IVUS) to overcome limitations existing in present three-dimensional reconstruction techniques using a method termed ANGUS. The IVUS data represent a cylindrical stack of cross-sections. A 3-D path of the catheter axis is reconstructed from two X-ray images, after which the stack of IVUS contours is wrapped around this 3-D catheter centerline. In order to establish the correct rotational position of the stack around the centerline, use is made of "landmarks" or catheter features which are visible in angiograms, as well as in a simulation of these angiograms derived from the reconstructed 3-D contour.

42 Claims, 8 Drawing Sheets

OTHER PUBLICATIONS

W. Li, J.G. Bosch, Y. Zhong, H. v. Urk, E.J. Gussenhoven, F. Mastik, F. v. Egmond, H. Rijsterborgh, J.H.C. Reiber, N. Bom, Image Segmentation and 3D Reconstruction of Intravascular Ultrasound Images, *Acoustical Imaging,* (1993) 20: 489–496 ed. Y. Wei and B. Gu, Plenum Press, New York.

M Laban, JA Oomen, CJ Slager, JJ Wentzel, R Krams, JCH Shuurbiers, A den Boer, C von Birgelen, PW Serruys, PJ de Feijter, "Angus: A new Approach to Three–Dimensional Reconstruction of Coronary Vessels by Combined Use of Angiography and Intravascular Ultrasound", *Computers in Cardiology 1995,* (Sep. 10–13, 1995) IEEE, 325–328.

CATHETER FOR OBTAINING THREE-DIMENSIONAL RECONSTRUCTION OF A VASCULAR LUMEN AND WALL

This is a continuation-in-part of copending U.S. application Ser. No. 08/600,140, filed Feb. 12, 1996, the contents of which are incorporated herein by reference.

FIELD OF THE INVENTION

This invention relates to ultrasound imaging of a body passageway, and particularly to a catheter system and methods for obtaining three-dimensional reconstruction of a vessel by X-ray angiography and intravascular ultrasound.

BACKGROUND OF THE INVENTION

From a sequence of IVUS images, acquired during automated, constant-speed pull-back, a 3-D image of a coronary artery can be reconstructed, by stacking the acquired frames along a straight axis. This kind of reconstruction is described in the literature (Roelandt et al., "Three dimensional reconstruction of intracoronary ultrasound images - Rationale, approaches, problems and directions," Circ. 90(2):1044–1055, (1994), this and all other references cited herein are expressly incorporated by reference as if fully set forth in their entirety herein) and some commercially available IVUS systems have such a possibility built in. However, in these images, the straight orientation of the vessel segment is a simplification, because the catheter tip will in reality traverse a spatial curve, the effect of which is hidden from the observer.

The approach of spatial curve reconstruction based on successive single point reconstructions of the catheter's tip trajectory has been chosen by many investigators. A recent article describing 3-D reconstruction based on McKay's algorithm for single point reconstruction is from: Evans et al., "Accurate three-dimensional reconstruction of intravascular ultrasound data," Circulation 93:567–576 (1996). In this article, it is described how, during pull-back, the echo transducer position is repetitively imaged (20–31 times) by biplane X-ray to determine a series of discrete positions of its 3-D path. The authors triggered for ECG and respiration to get similar vessel position at subsequent image acquisitions but, despite these measures, this method is prone to get artifacts because of differences in the respiratory and cardiac cycles. Furthermore, in the current reconstruction methods no solution has been provided to reconstruct the correct rotational orientation of the acquired cross-sectional images in the imaging plane once the position and orientation of the plane has been determined.

BRIEF SUMMARY OF THE INVENTION

To overcome these limitations, a method was developed using data obtained from ANGiography and intravascular UltraSound (ANGUS). Slager et al., The Thoraxcenter Journal 7/3:36–37 (1995). This technique provides real spatial geometry and orientation of a vessel, i.e., of the lumen and wall. The vessel is studied by IVUS during a pull-back of the IVUS catheter at a speed of, for example, 1 mm/s. Start and end of the pull-back are recorded by biplane fluoroscopy and, finally, biplane angiography is performed without changes in geometrical X-ray settings.

Using a computer program, the contours of the lumen-wall and wall-adventitia boundaries are semi-automatically detected at, for example, 0.5 mm intervals. Biplane fluoroscopy allows geometrical reconstruction of the catheter centerline, which, in the case of a sheath-based catheter, is the path of the IVUS transducer during pull-back. Combined use of the IVUS data, the catheter path, and the lumen contours in the biplane angiography provides a 3-D reconstruction of vessels without any evidence of an additional unknown geometric factor. Studying the trajectory in a vessel phantom of known dimensions a high accuracy was found (distance between reconstructed and real trajectory at any point <2 mm). First application in a human right coronary artery in vivo (length: 75 mm) showed a difference of 2% between the length of the reconstructed trajectory and the pull-back distance. Checking the locations of the origin of side branches in the 3-D reconstruction and biplane angiography, differences of less than 2 mm were found. Location and shape of stenoses in simulated projections of the reconstructed lumen matched well with biplane angiography. However, at the site of a previous PTCA, luminal haziness in angiography and dissection observed by IVUS may slightly reduce the accuracy of this technique.

Thus, combining X-ray ANGiography and intravascular Ultra-Sound (ANGUS) is a substantial improvement and provides a unique reconstruction of 3-D coronary geometry. In one method, X-ray angiography is combined with a stack of intravascular ultrasound (IVUS) images to obtain a 3-D reconstruction of a vessel. In another method, X-ray angiography is combined with "contour tracking" or border tracking as discussed in Li et al., "Image segmentation and 3D reconstruction of intravascular ultrasound images," In: "Acoustical Imaging," ed. Y. Wei and B. Gu, Plenum Press, New York (1993) to obtain a 3-D reconstruction of the vessel-blood interface and/or the wall-adventitia interface.

The present invention also contemplates a catheter system for imaging a vessel to obtain three-dimensional reconstruction, and which is specially adapted for ANGUS imaging in accordance with the invention. In one embodiment, the catheter system includes an elongate sheath having proximal and distal regions, wherein the distal region houses an ultrasound transducer regions, wherein the dist permits rotation and longitudinal translation in order to obtain a stack of two-dimensional or cross-sectional ultrasound images during pull-back. The sheath further comprises a series of radiopaque markers, wherein the number of markers is at least 3, more preferably at least 4, more preferably still at least 5, more preferably still at least 6, more preferably still at least 7, more preferably still at least 8, more preferably still at least 9, and still more preferably at least 10. The radiopaque markers are disposed about the distal region of the sheath and spaced by distances along the longitudinal centerline of 20 millimeters or less, more preferably 15 millimeters or less, more preferably 10 millimeters or less, more preferably 8 millimeters or less, more preferably 6 millimeters or less, and still more preferably 5 millimeters or less. The spacing distance between the markers determines the accuracy of path interpolation between successive markers. Because multiple scans will be obtained between successive markers when the markers are so spaced, a constant rate of pull-back or regular increments of pull-back can be used to allow calculation of the transducer position at each scan between markers.

The markers need not be equally spaced from one another, but in certain preferred embodiments, the markers are equally spaced along the longitudinal centerline. The radiopaque markers can be selected from any radiopaque materials well known in the art, and in preferred embodiments will comprise thin metal rings mounted on the distal region of the sheath. Alternatively, the radiopaque markers will consist of doping material incorporated into the distal region of the sheath. The markers are primarily intended to speed up the 3-D reconstruction of the catheter centerline which allows use on line and makes the method more robust. The markers allow use of a point reconstruction algorithm after which a line is interpolated through the reconstructed marker points.

In another embodiment, the markers are spaced in a manner that allows use of the effects of the markers in the ultrasonic images as an aid to provide positional feedback during pull-back. For this embodiment, the width of the markers should be no greater than 2 mm, more preferably 1 mm, more preferably 0.5 mm, more preferably 0.3 mm. The space left between markers should be at least 0.8 mm, more preferably 1 mm, more preferably 1.5 mm, more preferably 2 mm, more preferably 3 mm, and up to 20 mm in accordance with spacing as discussed elsewhere herein.

Where images are acquired at successive markers, the markers must be at least partially echotransparent. If the markers are only weakly radiopaque so as to be just visible, the echo-image behind the markers can be used; if the markers are not transparent, then the spaces in between the markers can be used for imaging. In this case, the spacing should at least allow the ultrasound beam to pass without causing reflections at the edges of the markers, so as to prevent interference of the markers with the beam.

In case of, for example, a manually-applied pull-back, close spacing of markers enables reconstruction of body passages in which no triggering of the pull-back is used. When using closely spaced markers, a loss in X-ray resolution by overlap of the markers may occur, especially where the centerline is viewed by X-ray at a sharp angle. Thus, it may be desired to highlight every fourth, sixth, eighth, or tenth marker so that the X-ray image can be used to reconstruct a path based on more widely spaced markers.

Figure 9A:
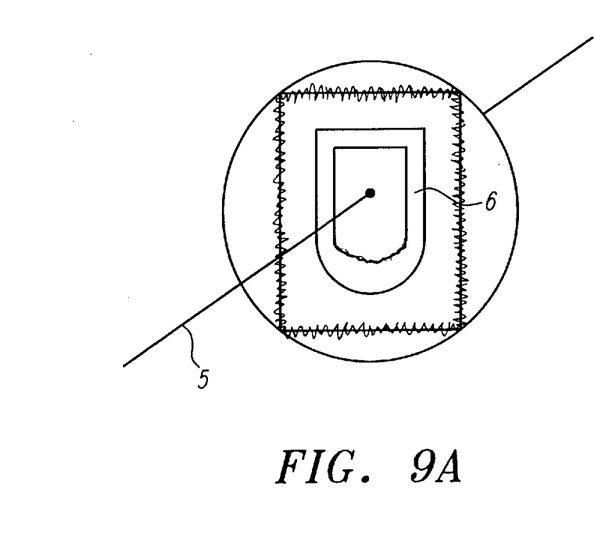
FIG. 9A depicts a single IVUS cross-sectional image which is positioned along the reconstructed centerline and oriented in a single imaging plane.
Figure 9B:
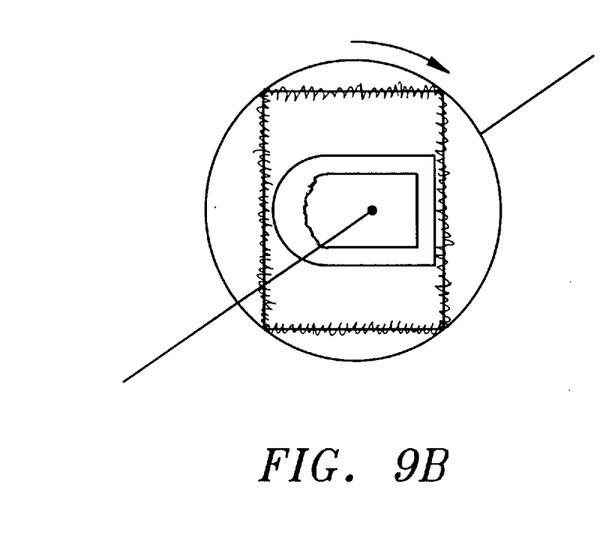
FIG. 9B shows adjustment of the rotational orientation of the IVUS image in the imaging plane.

During image reconstruction, a cross-sectional image is first placed at the correct position along the reconstructed centerline. Then, the image is oriented in a plane perpendicular to the centerline at that position. In a final step, the rotational orientation of the IVUS image in the imaging plane should be adjusted to obtain an optimal 3-D reconstruction. Adjustment of rotational orientation is illustrated in FIGS. 9A and 9B which show centerline 5 and cross-sectional image 6 at two different rotational orientations. In other preferred embodiments which permit rotational adjustment, the multiple markers on the sheath are arranged into a helical pattern, such that at least a one-half turn is obtained over the path being investigated. This allows the use of features of the X-ray image showing differences in opacity which is dependent on the intersection of the beams with the markers. Information thus obtained can be combined with features in the ultrasound image to deduce a correct rotational orientation of the ultrasound transducer in the imaging plane.

In other preferred embodiments, the distal region of the sheath includes at least one acoustical indexing marker which can optionally extend longitudinally parallel to the longitudinal centerline. The distal region of the sheath should be shaped to receive an imaging core comprising an ultrasound transducer operably disposed on a drive shaft or, optionally, an imaging catheter having an ultrasound transducer operably disposed at a distal region thereof. Where an imaging catheter is used in combination with the sheath, it is desirable that the imaging core, drive shaft, or imaging catheter be substantially more flexible than the elongate sheath. It is also desirable for the imaging core, drive shaft, or imaging catheter to include an opaque orientation marker which is radially fixed relative to the ultrasound transducer and which enables X-ray visualization of the rotational orientation of the transducer. In other embodiments, it is desirable for the transducer to further include a radiopaque component which enables visualization during the angiographic procedure.

In another preferred embodiment, the catheter system includes the components described above, except that the sheath having radiopaque markers is replaced by a sheath having a gradual change in X-ray radiopacity along the longitudinal centerline, this effect commonly known as a gray scale variation. In accordance with technology known in the art, gray scale radiopacity generally comprises doping material incorporated into the distal region of the sheath. In other preferred embodiments, the catheter system includes a sheath having at least one acoustical indexing marker disposed about the distal region, wherein the indexing marker preferably extends longitudinally parallel to the longitudinal centerline.

In another preferred embodiment, the catheter system includes an ultrasound transducer operably disposed on a drive shaft, wherein the drive shaft has a plurality of radiopaque markers disposed about the distal region of the drive shaft. The number of markers and the spacing are as described above. When the drive shaft is disposed in the sheath during operation, these markers will allow 3-D reconstruction of the catheter path. Marker arrangement in a helical pattern might be useful for reconstruction of the transducer rotational orientation.

In another preferred embodiment, the catheter system includes an elongate sheath and a guidewire operably disposed within the distal region of the sheath, wherein the guidewire has a longitudinal centerline and a plurality of radiopaque markers disposed about a region of the guidewire which can be positioned during angiography in an area of interest. In accordance with this embodiment, the guidewire may include 3, 4, 5, 6, 7, 8, 9, or more radiopaque markers, and the markers should be spaced by distances of no greater than 20 millimeters, more preferably no greater than 15 millimeters, more preferably no greater than 10 millimeter, more preferably no greater than 8 millimeters, more preferably no greater than 6 millimeters, and more preferably still no greater than 5 millimeters along the longitudinal centerline. Although the markers need not be separated by equally spaced distances along the longitudinal centerline, in preferred embodiments, the radiopaque markers are separated by equally spaced distances. The radiopaque markers may alternatively consist of thin metal rings mounted on the distal region of the guidewire, local attachment of radiopaque dots into the distal region of the guidewire, or a gray scale pattern as produced by doping material incorporated into the guidewire. In another embodiment, the catheter system includes at least one acoustical indexing marker disposed about the distal region of the sheath, and preferably extending longitudinally parallel to the longitudinal centerline. In the case of markers on the guidewire or on the drive shaft, the markers may consist of relatively wide bands having, for example, a width equal to the spacing distance between bands.

The present invention also includes methods for using a catheter having an ultrasound transducer and a longitudinal centerline in order to obtain accurate three-dimensional reconstruction of a body passageway, including a vessel. Such methods include the steps of obtaining a stack of cross-sectional ultrasound images, obtaining contours from those images at interfaces of different tissues, obtaining X-ray images of the catheter during pull-back, and combining the stack of cross-sectional ultrasound images and/or the derived interface contours with the geometry of the spatially reconstructed catheter longitudinal centerline thus determined to produce a reconstruction of a vessel. The three-dimensional geometry of the longitudinal centerline may be determined either by serial monoplane imaging or by obtaining a set of biplane X-ray images. In one preferred embodiment, the X-ray image acquisition of the centerline should be triggered by respiration and/or electrocardiogram. In another preferred embodiment, the ultrasound images are obtained at locations separated by equally spaced distances along the longitudinal centerline, such distances having a correlation to the location of each radiopaque marker along the catheter sheath. In other preferred embodiments, respiration-gated image acquisition and/or electrocardiographic-gated image acquisition is employed such that cardiac and respiratory movement are effectively eliminated in order to reduce distortions in the ultrasound images. During the cardiac and respiratory cycles, the catheter will periodically change location relative to the vessel. However, by gating the ultrasound image acquisition on both cycles, e.g., at end-diastole and end-expiration, it will be possible to capture images for which the three-dimensional location may be derived from the once recorded centerline location.

In another preferred embodiment, the pull-back may be applied step-wise each time after the ultrasound image has been acquired in an ECG and respiration triggered mode.

In another preferred embodiment, the stack of cross-sectional ultrasound images or contours is produced by placing individual frames of ultrasound images or contours derived from these images in correspondence with the geometry of the longitudinal centerline such that each frame lies in a plane disposed at a ninety degree (90) angle to the longitudinal centerline. When positioning the stack of cross-sectional images along the longitudinal centerline, it is preferred to determine the correct rotational position of the stack around the centerline. Landmarks within the vessel may be visible through X-ray contrast angiography and can be exploited for this purpose. Also, the position of the centerline relative to the lumen contrast contours should correspond with that of the centerline in the reconstruction relative to the reconstructed lumen border. Alternatively, an external ultrasound source with a known direction can be used to determine the correct rotational position because the external source provides direction-sensitive interference with the stack of ultrasound images obtained during pull-back.

DETAILED DESCRIPTION OF THE INVENTION

To improve on three-dimensional reconstruction of vessels, we added a method to reconstruct the spatial curve traversed by the catheter tip using a biplane X-ray image of the catheter at the start of the pull-back procedure.

We apply, as a first step, the same IVUS technology during an automated pull-back of a sheathed IVUS catheter at a speed of, for example, 1 mm/second or, in case of triggering by the ECG and respiration, in, for example, 1 mm steps. Start of the pull-back procedure is recorded by biplane X-ray. At least one set of biplane images should be acquired showing the catheter centerline at end-diastole and end-expiration. The IVUS catheter tip will follow the sheath closely during pull-back and the sheath itself will keep its relative position within the artery during this time. At the completion of the procedure, or just after the start of pull-back, biplane coronary angiography is performed without any change in geometrical X-ray settings. The biplane X-ray images, showing the catheter position shortly after start of pull-back, allow geometrical reconstruction of the position of the catheter's longitudinal centerline, which is assumed to represent the path of the catheter tip during pull-back.

From the IVUS images, end diastolic samples are selected and, from these, the contours of the lumen wall and external elastic membrane are semi-automatically detected (Li et al., "Image segmentation and 3D reconstruction of intravascular ultrasound images," In: "Acoustical Imaging," ed. Y. Wei and B. Gu, Plenum Press, New York (1993)). These contours are stacked and smoothed by removal of the higher frequency components using a 2 dimensional Fourier transform method.

Finally, these IVUS contours are combined with the reconstructed path of the catheter tip using the features of the angiograms like the position of the catheter centerline relative to the lumen border to establish the rotational position of the IVUS contours around the spatial curve.

A catheter for use herein will comprise an elongate sheath having proximal and distal ends and at least two regions: a proximal region and a distal region. The elongate sheath has a lumen which is shaped to house an ultrasound transducer in the distal region to permit both rotation of the transducer and longitudinal translation to permit ultrasound scanning of a region of a body passageway. Alternatively, the transducer may be carried by an imaging catheter comprising a removable imaging core as described in Sieben, U.S. Pat. No. 5,353,798, Crowley et al., U.S. Pat. No. 4,951,677, Griffith et al., U.S. Pat. No. 5,115,814, and Pomeranz, U.S. Pat. No. 5,095,911. The sheath further includes one or more radiopaque markers spaced along the longitudinal centerline of the sheath within the distal region to facilitate X-ray visualization while the catheter is operated within a body passageway. In another embodiment, the sheath operates with a guide wire in an over-the-wire design or in a monorail design as known in the art and described in Goodin et al., U.S. Pat. No. 4,928,693, Leary et al., U.S. Pat. No. 5,024, 234, Horzewski et al., U.S. Pat. No. 4,748,982, and Bonzel, U.S. Pat. No. 4,762,129, and the guidewire includes a plurality of radiopaque markers. Alternatively, the sheath may include a gradual change in X-ray radiopacity, such as a gray scale pattern, to indicate the position of the sheath during operation within a body passage-way.

In use, the catheter will be advanced into a patient's body passage-way until the distal region of the elongate sheath lies within a region of interest. A guidewire may be used to assist advancement of the catheter into the passage-way. The region of interest may be a region of a blood vessel which has been narrowed by a stenotic lesion. Once the catheter sheath is in place, in one embodiment the transducer is adjusted longitudinally so that it is aligned with a radiopaque marker, and preferably with the first or last marker where the sheath includes a plurality of markers. Such alignment can be achieved either by using ultrasound from the transducer to visualize the location of the marker, or by obtaining X-ray images of the catheter and aligning the marker with a radiopaque component fixed to the transducer. In another embodiment, such alignment is not required. Just making an X-ray of the catheter shows the different markers on the sheath as well as the position of the transducer or a radiopaque component fixed to the transducer. Reconstruction of the sheath markers in 3-D as well as the transducer position is then possible and the relative position of the transducer with respect to the sheath markers is known.

Where a determination of the rotational position of the stack of cross-sectional ultrasound images is desired, an angiographic dye may be injected into the vessel to permit X-ray imaging of the geometric contour of the passage-way. Dye injection is performed to show details of the coronary lumen and the relative position of the catheter centerline with respect to the lumen. When the imaging ultrasound catheter with its drive shaft is positioned in the sheath, imaging by X-ray clearly shows the catheter and its centerline, i.e., its drive shaft can clearly be indicated.

The transducer is pulled back at a constant rate of speed or stepped at equal distances in case of triggering by the electrocardiogram and/or respiration to obtain a sequence of cross-sectional ultrasound images which can be stacked to obtain a three-dimensional reconstruction. When using a procedure where the longitudinal position of the transducer is referenced only at the outset by a single marker, constant rate or equal step pull-back is important in order to accurately position each cross-sectional image along the path contour as determined from the X-ray images. A three-dimensional reconstruction of the vessel is then obtained by combining the stack of cross-sectional ultrasound images with the geometry of the longitudinal centerline as explained herein.

Where the sheath includes a plurality of markers, X-ray imaging at the beginning of pull-back allows determination of sheath markers as well as of any transducer (radiopaque) position in the sheath in biplane from which the transducer position and the marker positions in 3-D can be reconstructed. In the reconstruction, the cross-sectional ultrasound image captured at the moment of X-raying and/or the contour derived from it must just be positioned at the reconstructed transducer position. Other cross-sectional images and/or contours are stacked relative to this one at distances derived from the pull-back speed or from the increment of steps performed. This procedure may eventually be adjusted by using the information obtained from the ultrasound image at the position of the sheath markers. The latter may be at separation of distances of 20 millimeters or less, more preferably 15 millimeters or less, more preferably 10 millimeters or less, more preferably 8 millimeters or less, more preferably 6 millimeters or less, and still more preferably 5 millimeters or less.

In accordance with another embodiment, the transducer is first aligned with a radiopaque marker. Then, biplane X-ray imaging is applied to obtain a geometric reconstruction of the longitudinal centerline of the sheath, and ultrasound imaging with pull-back is used to obtain a stack of cross-sectional ultrasound images. Ultrasound data is collected and saved at intervals when the transducer reaches each successive radiopaque marker. Although the markers need not be equally spaced, it is preferred that they are. The width of the markers should be no greater than 2 mm, more preferably 1 mm, more preferably 0.5 mm, more preferably 0.3 mm. The space left between markers should be at least 0.8 mm, more preferably 1 mm, more preferably 1.5 mm, more preferably 2 mm, more preferably 3 mm, and up to 20 mm in accordance with spacing as discussed elsewhere herein.

Where images are acquired at successive markers, the markers must be at least partially echotransparent. If the markers are only weakly radiopaque so as to be just visible, the echo-image behind the markers can be used; if the markers are not transparent, then the spaces in between the markers can be used for imaging. In this case, the spacing should at least allow the ultrasound beam to pass without causing reflections at the edges of the markers, so as to prevent interference of the markers with the beam. In case of, for example, a manually-applied pull-back, close spacing of markers enables reconstruction of body passages in which no triggering of the pull-back is used. When using closely spaced markers, a loss in X-ray resolution or overlap of the markers may occur, especially where the centerline is viewed by X-ray at a sharp angle. Thus, it may be desired to highlight every fourth, sixth, eighth, or tenth marker so that the X-ray image can be used to reconstruct a path based on more widely spaced markers.

After a stack of two-dimensional ultrasound images is obtained and/or the contours at the lumen wall and wall-tissue border have been determined, a three-dimensional reconstruction of the interior lumen and wall/tissue environment of a body passageway is produced by combining the stack of cross-sectional images and/or the contours with the geometry of the longitudinal centerline of the sheath, which approximates the geometry of the path followed by the ultrasound transducer. First, the geometry of the longitudinal centerline is determined from the X-ray image data. The spatial position of a single Roentgen-opaque marker-point registered by a biplane X-ray imaging unit can be reconstructed from its two projections. Two slightly different methods exist for such reconstruction. First, during image acquisition, the position of the image intensifier entrance screen and X-ray focus are registered in an x, y, z coordinate system defined in the room containing the imaging equipment. The geometric enlargement of the imaging chain from image intensifier entrance screen up to the final digitized computer image is calibrated by imaging a calibration grid at the entrance screen having exactly known dimensions. From the registered geometrical coordinates and the calibration data, the relationship between the coordinates a marker-point in space and its coordinates in the biplane projections can be mathematically derived using well-known mathematical techniques. This implies that when the coordinates of a point in its two projections are known, the spatial coordinates in x, y, z can be determined. See, e.g., "Image reconstruction from biplane angiographic projections," Dumay, A.C.M., Ph.D. Thesis, Technical University Delft (1992), ISBN 90-9005432-4.

A second method for point reconstruction, slightly different from the above, uses a calibration cube containing multiple radiopaque markers with known positions. This technique does not make use of a registration of the position of the X-ray focus and image intensifier entrance screen. For a certain position and orientation of the imaging chain's components, it uses the two projection images of the cube's markers to determine a transformation matrix describing the relation between the spatial coordinates of a marker and its coordinates in the projection images. Using the inverse of this matrix, the spatial position of a marker imaged by the identically-oriented imaging chain can be reconstructed from its coordinates as derived from both projections. See, e.g., McKay et al., "Graphic methods for tracking three-dimensional heart wall motion," Comput. Biomed. Res. 15:455–473 (1982).

In another ANGUS approach not requiring a plurality of markers along a centerline, a single pair of images (simultaneous biplane or sequential monoplane) showing the catheter's imaging core is used to reconstruct the complete pull-back path. These images are taken at end-expiration and end-diastole. Digitization of the catheter images involves indication of the catheter centerline in both projections. These lines are stored as a series of positions in a computer. The digitized positions in the different projections cannot be simply paired as the catheter images do not provide unique points which can be identified in both projections. Only two unique points, i.e., the echotransducer position and the catheter tip, can be identified in both projections. Therefore, in this case, we need a slightly different approach to reconstruct a spatial curve representing the catheter's centerline covering the complete pull-back trajectory. For this reconstruction of the catheter path from its projections, we apply routines written in MATLAB (The Math Works, Inc., Cochituate Place, 24 Prime Park Way, Natick, Mass.) language. A more detailed description of the applied algorithms is described in Laban et al., "ANGUS: A new approach to three-dimensional reconstruction of coronary vessels by combined use of angiography and intravascular ultrasound," Computers in Cardiology, IEEE Comp. Soc., 325–328, (1995). Briefly, we make a reasonable description of some spatial curve in Fourier parameter description which represents a first approximation of the searched catheter centerline in the x, y, z space. The projection images of this centerline are next calculated using the inverse of one of the two-point reconstruction methods described above. In the projection plane, a comparison is being made between the projections of the first centerline approximation and the actual digitized centerline projections. On base of this comparison, a cost function is defined which accounts for the differences between the projections. Then a correction is applied on the parameter description to improve matching of the simulated and the real projections. In a series of subsequently improved approximations, the cost function will be minimized until an accurate description of the catheter in 3-D is obtained. Additional information obtained from the uniquely defined position of the imaging transducer enables the selection of a specific point on this curve, i.e., the position of the crystal at the moment of X-ray application. From this point, subsequent transducer positions during pull-back can be derived as the pull-back is performed by a precisely controlled motorized system.

For vessel reconstructions to be used for quantitative purposes, we combine a stack of cross-sectional border lines at the lumen wall and wall adventitia interface derived from intravascular images which were captured during pull-back. Each cross-sectional contour belonging to an imaging plane has to be positioned in the x, y, z space on the reconstructed catheter centerline. The location of the imaging plane is derived from the pull-back speed and the uniquely X-ray-registered transducer position. The orientation of the image plane is chosen perpendicular to the centerline. Finally, the rotational position of the contour in the imaging plane has to be determined (FIGS. 9A and 9B). The latter is described in more detail in Laban et al., "ANGUS: A new approach to three-dimensional reconstruction of coronary vessels by combined use of angiography and intravascular ultrasound," Computers in Cardiology, IEEE Comp. Soc., 325–328, (1995), and Slager et al., "Three-dimensional geometry and orientation of coronary lumen and plaque. Reconstruction from angiography and ICUS (ANGUS)," Thoraxcenter Journal, pages 36–37 (1995), and includes a path dependent correction for twisting of the catheter which introduces a change in the rotation of the contours between successive cross-sections. The optimal rotational position is determined at hand of a comparison with the biplane contrastangiograms which have been taken during pull-back at end diastole and end respiration. These contrastangiograms show the position of the intravascular imaging catheter relative to the vessel lumen and the vessel lumen itself over a few cardiac cycles. For the selected geometry of the applied X-ray projections, corresponding shadow images of the reconstructed lumen borders and the catheter centerline are calculated for a set of rotational positions of the cross-sectional images. By comparing those images with the contrastangiograms, the optimal rotational position can be selected.

In alternative embodiments, angiography may be omitted if the radial position of the stack of images around the reconstructed longitudinal centerline can be derived from, for example, the helical arrangement of the sheath markers, or from the radial orientation of a radiopaque element (for example, a small opaque disk), radially fixed to the transducer. Such an element can be documented during rotation by X-ray filming. Orientation of the element can thus be derived from the X-ray images and used to determine the orientation of the simultaneously captured ultrasound cross-sectional images.

Using a catheter with multiple sleeve or sheath markers provides an improvement to the latter-described method and enables on-line application of 3-D path reconstruction. Using either of the reconstruction methods described above, the x, y, z position of individual markers can be reconstructed from the projection images. Subsequently, an approximated catheter centerline can be calculated by applying a spline (standard math lab routine) fitting through these points.

Figure 1:
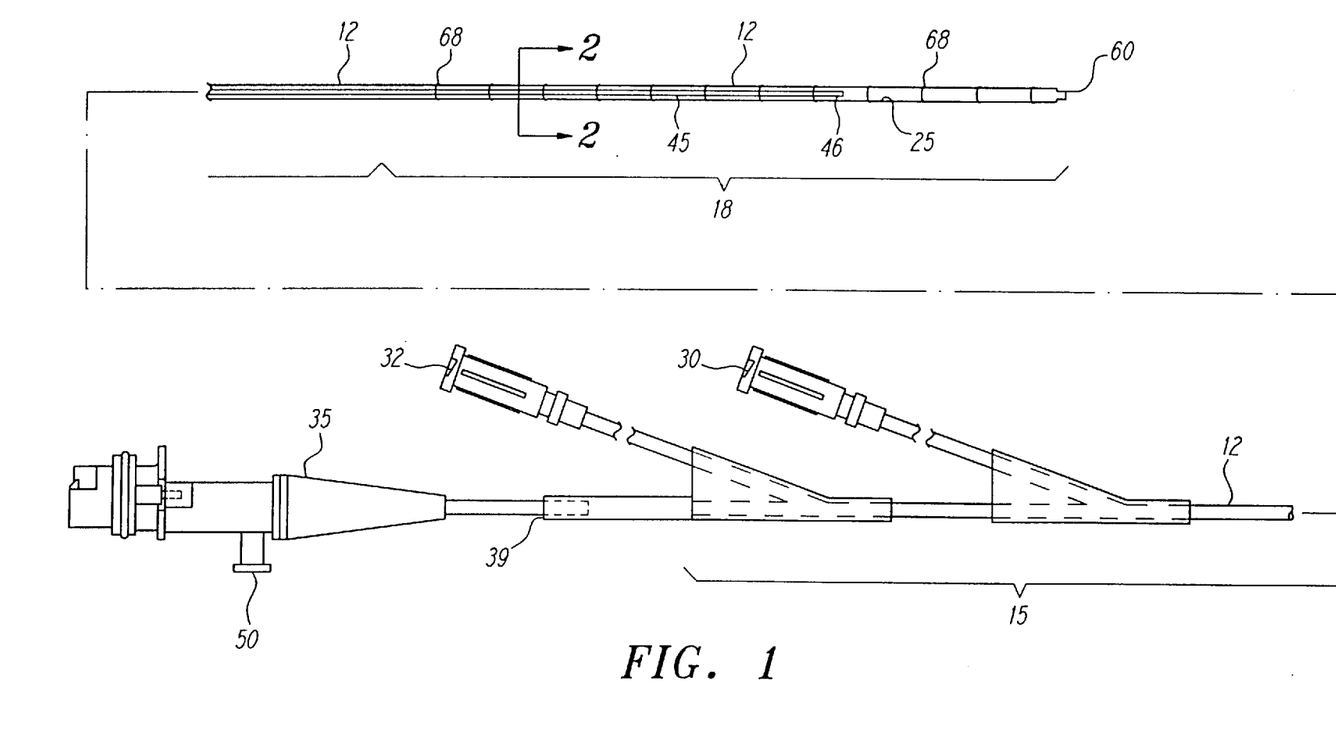
FIG. 1 depicts a preferred embodiment of a catheter according to the present invention.
Figure 2A:
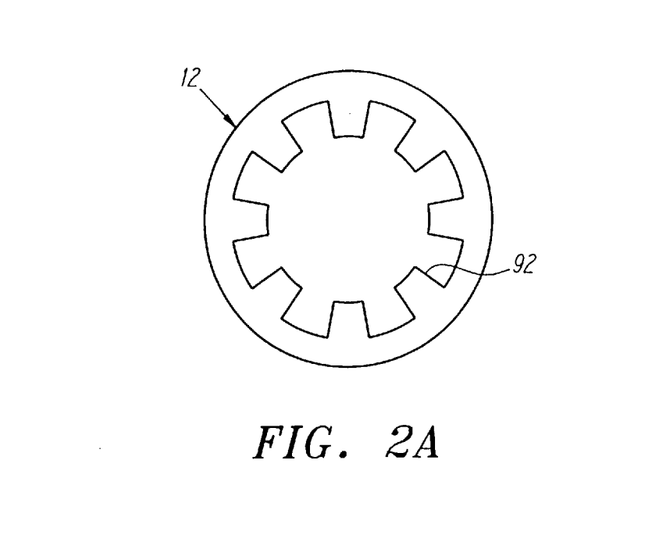
FIG. 2A is a cross-sectional view through section line 2–2 of the catheter depicted in FIG. 1.
Figure 2B:
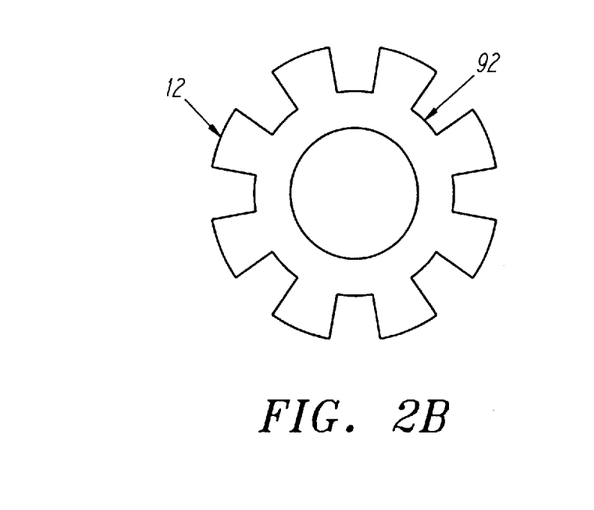
FIG. 2B is an alternative cross-sectional view through section line 2—2 of the catheter depicted in FIG. 1.

FIG. 1 depicts one example of a preferred catheter for use in accordance with methods disclosed herein. The catheter has an elongate sheath 12, which comprises proximal region 15 and distal region 18. FIGS. 2A and 2B are cross-sectional views of the distal region of sheath 12 through section line 2—2 according to alternative embodiments. Guidewire port 30 and work element port 32 (FIG. 1) place lumen 25 in communication with the exterior of the catheter near its proximal end. Drive shaft 45 is reciprocatably disposed within lumen 25, and carries ultrasound transducer 46 at its distal tip. (For clarity, only the distal portion of drive shaft 45 is illustrated.) At its proximal end, lumen 25 is in communication with expandable member 39, which is connected in turn to proximal housing 35. The proximal housing is adapted to connect a proximal end of drive shaft 45 to a drive motor (not shown) for rotating the drive shaft. Expandable member 39 allows the drive shaft to be advanced and retracted within lumen 25 by moving proximal housing 35 with respect to the elongate sheath to lengthen or shorten expandable member 39 as desired. The construction and use of proximal housing 35 is fully described in Salmon et al., U.S. Pat. No. 5,314,408.

The distal region 18 of sheath 12 includes a distal tip 60 and radiopaque markers 68 wrapped around or integral with sheath 12 to enable fluoroscopic imaging to assist in determining the geometry of the longitudinal centerline of the sheath. Because these markers are also visible by ultrasound, these markers enable the operator to correlate the transducer position relative to each marker for each image with a precise anatomical/vessel location as determined fluoroscopically. The length of distal region 18 will generally be between 5 and 30 centimeters, and the minimum width crossable by the elongate sheath will typically be in the range of 0.020–0.045 inches. The foregoing ranges are intended only to illustrate typical device dimensions, and the actual dimensions may obviously vary outside of the stated ranges without departing from the basic principles disclosed herein.

A cross-section through distal region 18 of sheath 12 through line 2—2 is depicted in FIGS. 2A and 2B. As can be seen therein, acoustical indexing markers or rotational compensation markers 92 can be incorporated circumferentially into the wall of sheath 12 in the distal region 18. The markers 92 may be splines or patterns incorporated on the interior surface of sheath 12, as depicted in FIG. 2A, or on the exterior surface of the sheath, as depicted in FIG. 2B. The inclusion of acoustical indexing markers and the considerations therefore are fully discussed in Sieben et al., U.S. Pat. No. 5,243,988, and will not be repeated here.

Figure 3:
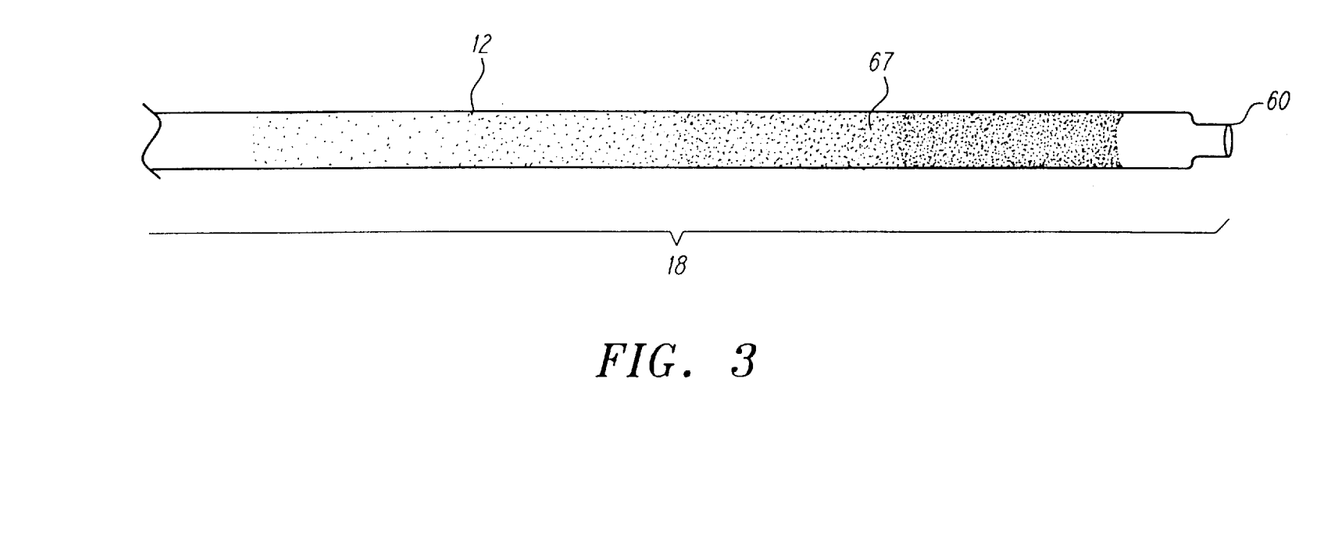
FIG. 3 depicts an alternative distal region of the catheter depicted in FIG. 1.

FIG. 3 depicts an alternative embodiment which shows the distal region 18 of sheath 12 having distal tip 60. In this embodiment, the radiopaque metallic rings are replaced by a gray scale pattern 67, or other pattern to indicate a change in position between the sheath and the transducer. The pattern can be applied over just the distal length 18 on the sheath, or over the entire length. Such patterns are fully discussed in Sieben et al., U.S. Pat. No. 5,243,988.

Figure 4:
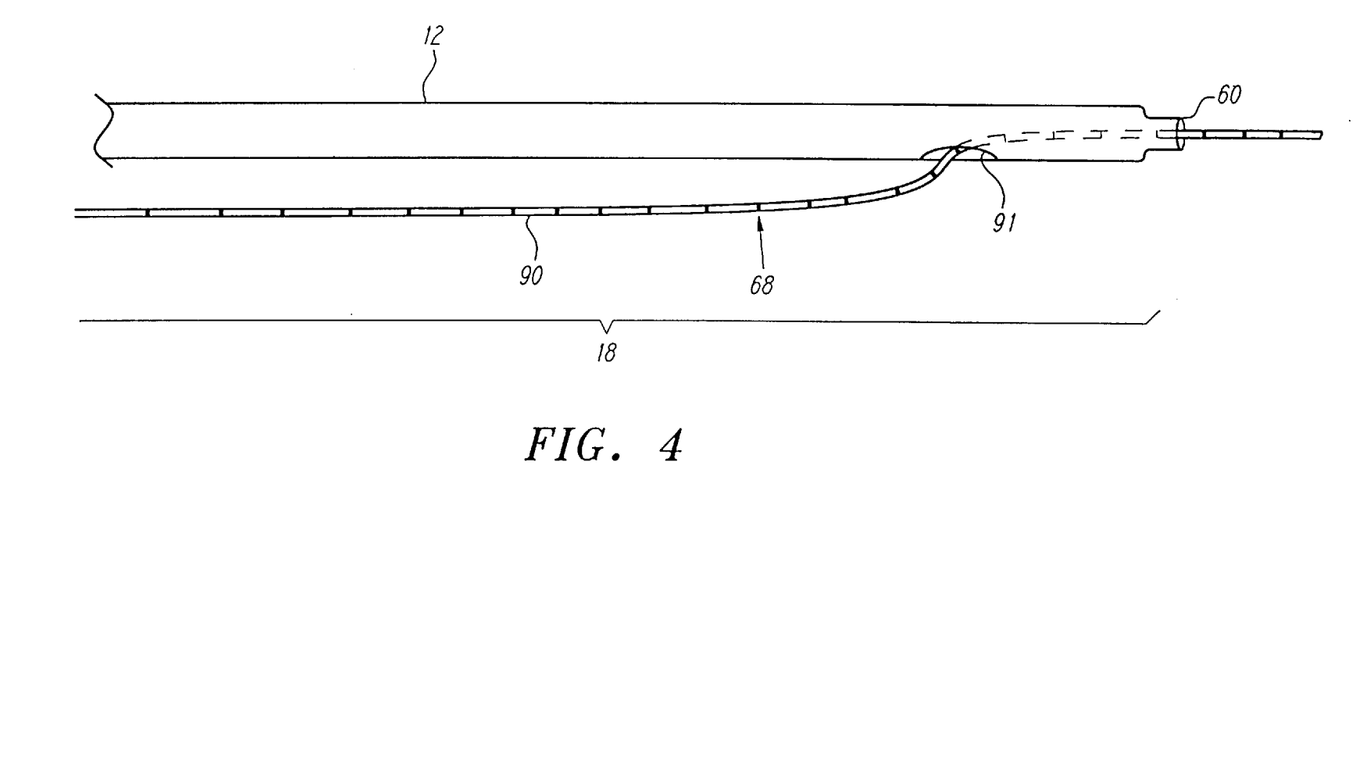
FIG. 4 depicts an alternative distal region of the catheter depicted in FIG. 1.

FIG. 4 depicts an alternative embodiment which shows distal region 18 of sheath 12 having distal tip 60. This sheath would permit "monorail" operation as known and discussed in the art. During use, guide wire 90 passes through aperture 91 located proximal of distal tip 60 and distal of proximal region 15 of the elongate sheath 12. The guidewire 90 includes one or more radiopaque markers 68, or a gray scale pattern, which facilitate both geometry mapping by fluoroscopy and determination of transducer position relative to each marker during ultrasound imaging. As discussed above, angiography can be used to fluoroscopically determine vessel geometry. It is apparent that acoustical indexing can be used with the FIG. 4 embodiment to further improve three-dimensional reconstruction by allowing the operator to determine the correct rotational position of the stack of cross-sectional images around the longitudinal centerline of the sheath.

A guidewire with radiopaque markers and imaging catheter/core can be used also in an over-the-wire approach as follows: After the imaging catheter/core is retracted from the sheath and stored in the "main" catheter, the marked guidewire can be disposed in the sheath and thus provide a series of markers inside the sheath. These markers can be used to reconstruct the 3-D position of the sheath by the biplane X-ray reconstruction method. After this procedure, the imaging catheter is disposed in the sheath and one more X-ray image at the beginning of pull-back will enable reconstruction of the position of the ultrasonic transducer. Subsequent transducer positions may be derived from the applied speed of the pull-back.

EXAMPLE 1 Processing the IVUS Images

The IVUS images are recorded during automated pull-back on a PAL standard S-VHS video tape, resulting in 25 images/second. Other means of pull-back can also be used, e.g., by applying equidistant pull-back steps triggered by ECG. A few seconds after pull-back has started, a short biplane X-ray film is made and the start of this film is marked on the audio track of the S-VHS tape to enable synchronization with the IVUS contours sequence. The IVUS picture to be selected is augmented with a marker which indicates the occurrence of the R-peak in the patient's ECG.

By filming the position of the catheter shortly after start of pull-back, any backlash that the automatic pull-back system might experience has disappeared and a precise relation between the echo image location in the filmed biplane images and the recorded IVUS pictures can be established. This is done by locating the ultrasound transducer or the catheter tip as seen in both of the biplane film images.

Following the acquisition, the S-VHS images are semi-automatically processed (Roelandt et al., "Three dimensional reconstruction of intracoronary ultrasound images - Rationale, approaches, problems and directions," Circ. 90(2):1044–1055, (1994)) to detect the contour of both the lumen and the external elastic membrane. Only images containing the R-peak marker are selected, thus restricting analysis to the end-diastolic shape of the artery. The X, Y positions of the detected points are transferred to a file, together with the R—R interval. The time at which each image was recorded is interpreted as Z-axis value, making use of the fact that the intravascular ultrasound catheter moved at constant speed through the artery.

Figure 5:
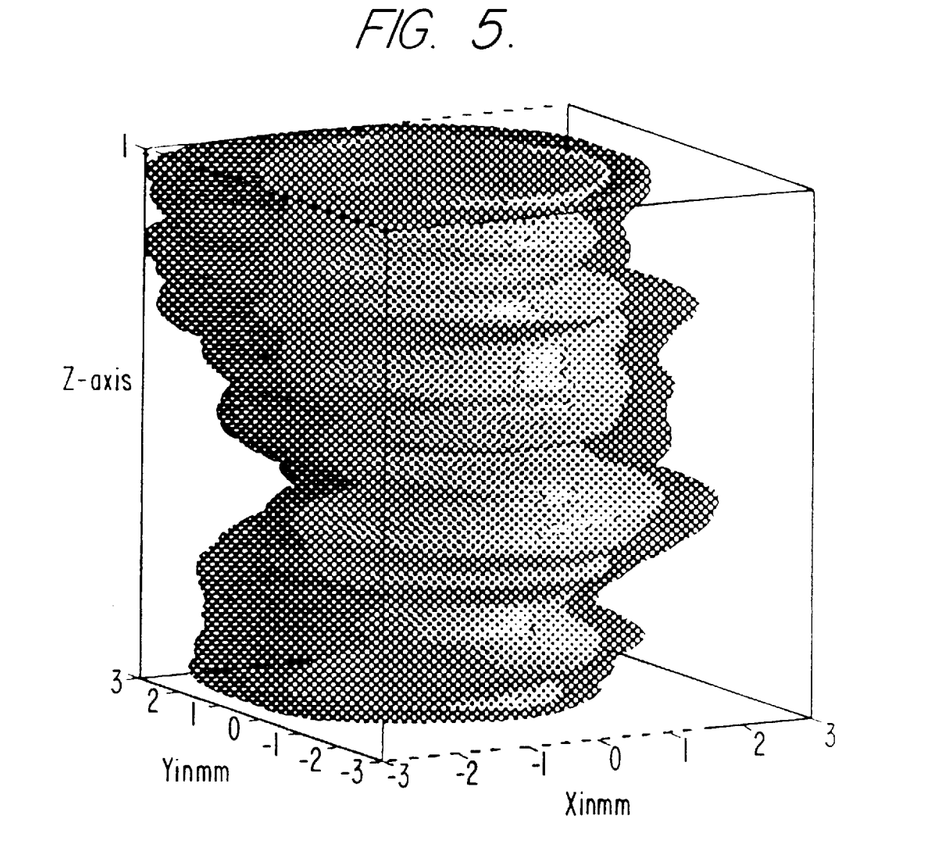
FIG. 5 is a 3-D view of the stack of smoothed IVUS cross-sections (Z-axis not to scale). Dark surface: external elastic membrane; light surface: vessel lumen.

Using MATLAB, a numeric computation and visualization program, the collected points are resampled at a constant Z-axis interval of 1 second, which translates into 1 millimeter distances between successive cross-sectional images. The contour data are subsequently converted to cylindrical coordinates, thus expressing the vessel wall, as well as the external elastic membrane by $r=f(\phi, z)$, where r=radius; $\phi$=angle, and z=position along Z-axis. Next, a smoothing algorithm is applied to the surface $f(\phi, z)$ by removing the higher frequency components of its 2D Fourier transform. The final result is a stack of IVUS cross-sectional images (FIG. 5), all aligned perpendicular to and centered around the Z-axis.

EXAMPLE 2 Reconstruction of the Centerline

In order to achieve a true 3-D reconstruction of the shape of the vessel, we need to assess the real 3-D path of the IVUS catheter tip. In order to do so, we produce two pictures, showing both of the biplane X-ray images with the position of the IVUS catheter at the start of the pull-back procedure. As stated before, we may assume that the trajectory projections followed by the catheter tip closely coincide with the centerline of the catheter image in its biplane projections.

An alternative to this method would be to record the trajectory of the tip by filming its position many times during pull-back. An investigation of this method showed that a considerable amount of additional movement is superimposed on the catheter path, even when gating for respiration and heart contraction. Therefore, this method is deemed to be less desirable.

After digitization of the biplane projections using a custom-built program, MATLAB routines are used to perform the necessary calculations to reconstruct the true 3-D path of the catheter from its biplane shadow images. A first 3-D guess is described in Fourier parameter form. Using an independent variable ($0 \leq s \leq 1$), the catheter centerline $R(s)$ can be described by:

$$\overline{R}(s) = \overline{a} + \overline{b}.s + \overline{c} \cdot \sin(2\pi.s) + \overline{d} \cdot \cos(2\pi.s) + \overline{e} \cdot \sin(4\pi.s) + \overline{f} \cdot \cos(4\pi.s) + \ldots$$

Using a Gauss-Newton optimization method, the parameter vectors $\overline{a}, \overline{b}, \overline{c}, \overline{d}, \overline{e}, \overline{f}$ . . . are adjusted, such that the projection of the 'guessed' 3-D curve onto each of the image intensifier planes coincides as closely as possible, according to a minimum cost algorithm, with the filmed images of the IVUS catheter centerline.

Although it can be shown that not all possible curves can be reconstructed in this way, due to the existence of 'blind planes': planes that are perpendicular to both of the image intensifier entrance screens, with some caution and experience, it is possible to select a constellation of both image intensifier planes, such that sections of the curve in the 'blind' position are avoided.

EXAMPLE 3 Combination of Angio and IVUS Data

Figure 6:
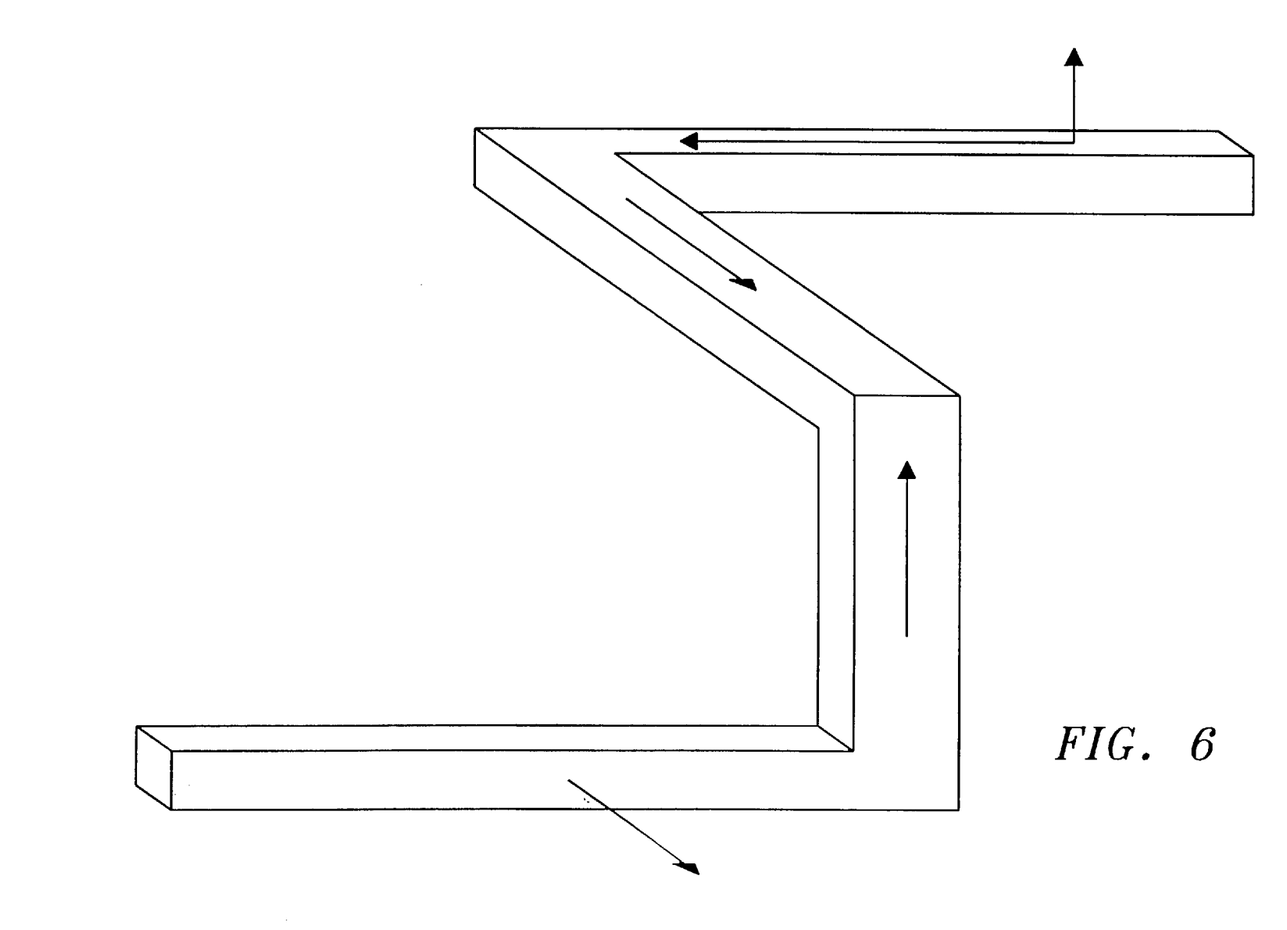
FIG. 6 shows how the twist of catheter tip depends on the course of the spatial curve. The top point at 12 o'clock has become the forward point at 9 o'clock.

After having acquired a stack of cross-sections as described in Example 1, and a 3-D centerline as described in Example 2, the stack has to be 'fitted' around the centerline. Because the start signal from the fluoroscopy film camera is recorded on the audio track of the IVUS VHS video, the position of the stack along the centerline is known. It is also known that the resampled stack of cross-sectional images contains pictures at 1 millimeter intervals, measured along the centerline. Two different unknowns, however, have still to be taken into account:

a) Under certain conditions, the catheter tip will exhibit a twist with respect to an external, fixed system of axes (FIG. 6).

b) The rotational position of the stack of images is unknown.

The effect under (a) can be explained as follows. If the catheter itself is assumed to be torsion free, the catheter tip will twist if the curve enters another plane. The amount of twist can be found from the Frenet formulas (Davis et al., "Introduction to Vector Analysis," Wm. C. Brown Publishers, 86:88 (1988)), from which it can be derived that the tip will rotate if the third derivative ($d^3 R/ds^3$) of the parametric curve R(s) does have a non-zero component in a direction perpendicular to both T and N, where T denotes the tangent (T=dR/ds) to the curve R(s) and N denotes the normal (N=dT/ds) to the curve R. Knowing this, one can devise an algorithm that takes this relative rotation, i.e., the rotation from one cross-sectional image to the next, into account. The algorithm we use to reconstruct the 3-D vessel by wrapping successive cross-sectional IVUS images around the reconstructed 3-D catheter centerline, takes the relative rotational differences between successive cross-sections into account by considering the change in local radius of the computed catheter centerline.

This finally leaves us with the problem mentioned under (b). Although the rotation of each vessel cross-section is known with respect to the former one, the rotational position of the first cross-section remains unknown. If we change the rotational position of the first cross-sectional image around the catheter centerline, the whole of the vessel wall will rotate around the fixed and curved centerline. We refer to this phenomenon as 'sock rotation,' because of the similarity of the situation with a sock on a leg.

In order to assess the correct sock rotation, the reconstruction of the 3-D vessel wall is computed for all sock rotations between 0° and 360° in 10° steps. The 2 biplane projections of these 3-D reconstructions also showing the projected centerline reconstruction are then computed resulting in 36 reconstructed biplane frames. While single stepping forward and backward through this sequence of pictures, a comparison is made between each of the computed pictures and the biplane angio as recorded at the end of the pull-back procedure. Because real vessels always exhibit landmarks in the form of irregularities, side branches, and bends, and moreover, the catheter position relative to the vessel wall varies throughout the pull-back, the most suitable sock rotation can be estimated from this procedure.

A final computation is then made to arrive at a full 3-D reconstruction of the vessel.

EXAMPLE 4 Phantom Study

In order to assess the accuracy of the method described here, a phantom has been constructed, consisting of a plastic cylinder with a diameter of 120 mm, into which we cut a helical groove, with a width of 3 mm and a depth of 3 mm. The bottom of the groove is semicircular. The pitch of the groove is 100 mm for one complete 360° turn. The groove exhibits a D-shaped cross-section. The groove was filled with saline diluted contrast medium and the aforementioned protocol was followed to obtain the IVUS images and the biplane X-ray pictures from this phantom.

Figure 7:
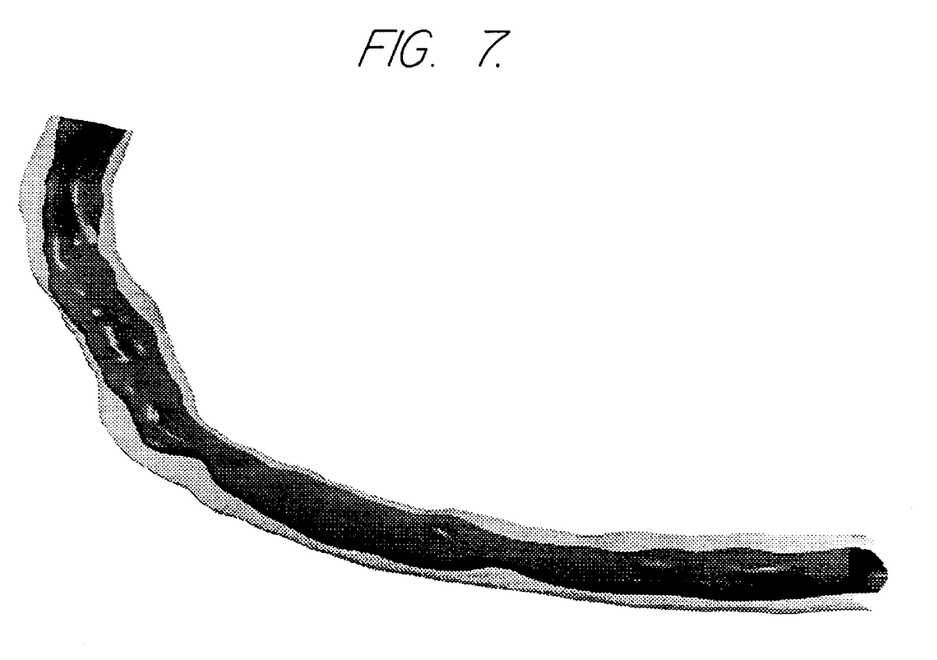
FIG. 7 is a rendering of a reconstructed in vivo vessel.

Studying the trajectory within this phantom, a high accuracy was found, with a distance between real and reconstructed trajectory <1 mm. First application in a human right coronary artery in vivo (length: 75 mm) showed a difference of 2% between the length of the reconstructed trajectory and the pull-back distance. Location and shape of stenoses in simulated projections of the 3-D reconstructed lumen matched well with biplane angiography (FIG. 7).

In using the method as described herein, it is desired to have a high degree of accuracy from the biplane X-ray installation. We found that errors like non-coinciding iso-centers (distance ≈2 mm) and a rotation of the image by the intensifier (≈3°) influenced the results noticeably. Nevertheless, due to the best fit nature of the minimum cost algorithm that is used, we achieved satisfying results with our first clinical trials.

Figure 8:
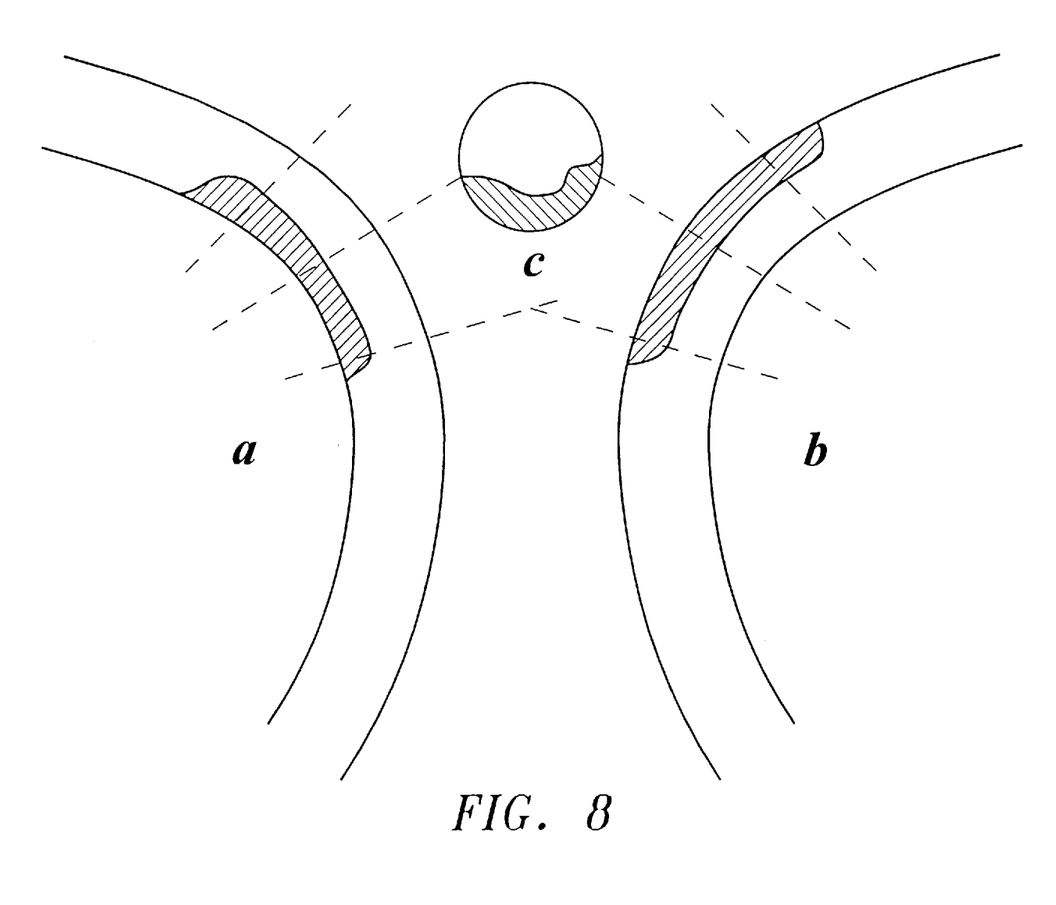
FIG. 8 shows how the position of a sclerotic plaque in an inside bend (a) or outside bend (b) influences its extent, without a marked change in IVUS image (c)

The advantage of the described method above the common cylindrical straight reconstruction can be appreciated if one considers, for instance, the problem of estimating the extent of plaque material. Although IVUS will allow an estimation of the thickness of the plaque material, when calculating a volumetric estimate of sclerotic material, one should take the position of the plaque relative to the bend of the vessel into account (FIG. 8).

This reconstruction method might also find use in studies where one attempts to reconstruct the flow pattern in diseased arteries using finite element analysis.

Modifications and variations of the present invention, and methods of use thereof, will be obvious to those skilled in the art from the foregoing detailed description. Such modifications and variations are intended to come within the scope of the appended claims.

What is claimed is:

1. A catheter for imaging a vessel to obtain three-dimensional reconstruction of a lumen of the vessel in a region of interest, said catheter comprising:

an elongate sheath having proximal and distal regions, said distal region adapted to enter the vessel while said proximal region extends outside of the vessel to permit control of said catheter, said distal region further adapted to receive an ultrasound transducer and to permit rotation of said transducer, and simultaneous longitudinal translation of said transducer relative to said sheath alonge a pull-back trajectory to obtain a stack of images during pull-back; and at least four radiopaque markers disposed about the distal region of said sheath, wherein said markers enable determination of the pull-back trajectory in the region of interest.

2. The catheter of claim 1, wherein said radiopaque markers are separated by equally spaced distances along the catheter longitudinal centerline.

3. The catheter of claim 1, wherein said radiopaque markers comprise thin metal rings mounted on the distal region of said sheath.

4. The catheter of claim 1, wherein said radiopaque markers are arranged in a helical pattern along said elongate sheath.

5. The catheter of claim 1, further comprising at least one acoustical indexing marker disposed about the distal region of said sheath.

6. The catheter of claim 5, wherein said acoustical indexing marker extends longitudinally parallel to the catheter longitudinal centerline.

7. The catheter of claim 1, wherein the markers are spaced by distances of no greater than 20 millimeters as measured along the catheter longitudinal centerline.

8. The catheter of claim 1, wherein the markers are spaced by distances of no less than 0.8 millimeters as measured along the catheter longitudinal centerline.

9. The catheter of claim 1, wherein the markers are on said sheath.

10. The catheter of claim 1, further comprising a guidewire operably disposed within the distal region of said sheath, wherein the markers are on said guidewire.

11. The catheter of claim 1, further comprising a drive shaft operably connected to the ultrasound transducer, wherein the markers are on said drive shaft.

12. The catheter of claim 1, wherein the markers are disposed about a region of said sheath which lies within the vessel at the region of interest and overlaps longitudinally with a segment of the pull-back trajectory.

13. The catheter of claim 1, further comprising an imaging core or imaging catheter adapted to operate within said elongate sheath, said imaging core or catheter having an ultrasound transducer operably disposed at a distal region thereof.

14. The catheter of claim 13, wherein said imaging core or imaging catheter is substantially more flexible than said elongate sheath.

15. The catheter of claim 13, wherein said imaging core or imaging catheter further includes an angiographic orientation marker which is radially fixed relative to said ultrasound transducer to permit X-ray visualization of rotational orientation of said ultrasound transducer.

16. The catheter of claim 13, wherein said transducer further includes a radiopaque component.

17. A catheter for imaging a vessel to obtain three-dimensional reconstruction of a lumen of the vessel in a region of interest, said catheter comprising:

an elongate sheath having proximal and distal regions, said distal region adapted to enter the vessel while said proximal region extends outside of the vessel to permit control of said catheter, said distal region further adapted to receive an ultrasound transducer and to permit rotation of said transducer, and simultaneous longitudinal translation of said transducer relative to said sheath alonge a pull-back trajectory to obtain a stack of images during pull-back; and said catheter having associated therewith a gradual change in X-ray radiopacity extending longitudinally along a distal region thereof, wherein said change in radiopacity enables determination of the pull-back trajectory in the region of interest.

18. The catheter of claim 17, wherein said gradual change in X-ray radiopacity comprises doping material incorporated into the distal region of said sheath.

19. The catheter of claim 17, further comprising at least one acoustical indexing marker disposed about the distal region of said sheath.

20. The catheter of claim 19, wherein said acoustical indexing marker extends longitudinally parallel to the catheter longitudinal centerline.

21. The catheter of claim 17, wherein said change in radiopacity is on said sheath.

22. The catheter of claim 17, further comprising a guidewire operably disposed within the distal region of said sheath, wherein the change in radiopacity is on said guidewire.

23. The catheter of claim 17, further comprising a drive shaft operably connected to the ultrasound transducer, wherein the change in radiopacity is on said drive shaft.

24. The catheter of claim 17, wherein the change in radiopacity occurs about a region of said sheath which lies within the vessel at the region of interest and overlaps longitudinally with a segment of the pull-back trajectory.

25. A catheter for imaging a vessel to obtain three-dimensional reconstruction of a lumen of the vessel in a region of interest, said catheter comprising:

an elongate sheath having proximal and distal regions, said distal region adapted to enter the vessel while said proximal region extends outside of the vessel to permit control of said catheter, said distal region further adapted to receive an ultrasound transducer and to permit rotation of said transducer, and simultaneous longitudinal translation of said transducer relative to said sheath along a pull-back trajectory to obtain a stack of images during pull-back;

a guidewire operably disposed within said distal region of said elongate sheath; and at least four radiopaque markers disposed about a distal region of said guidewire, wherein said markers enable determination of the pull-back trajectory in the region of interest.

26. The catheter of claim 25, wherein said radiopaque markers are separated by equally spaced distances along the catheter longitudinal centerline.

27. The catheter of claim 25, wherein said radiopaque markers comprise thin metal rings mounted on the distal region of said guidewire.

28. The catheter of claim 25, further comprising at least one acoustical indexing marker disposed about the distal region of said sheath.

29. The catheter of claim 28, wherein said acoustical indexing marker extends longitudinally parallel to the catheter longitudinal centerline.

30. The catheter of claim 25, wherein the markers are spaced by distances of no greater than 20 millimeters as measured along the catheter longitudinal centerline.

31. The catheter of claim 25, wherein the markers are spaced by distances of no less than 0.8 millimeters as measured along the catheter longitudinal centerline.

32. A catheter for imaging a vessel to obtain three-dimensional reconstruction of a lumen of the vessel in a region of interest, said catheter comprising:

an elongate sheath having proximal and distal regions, said distal region adapted to enter the vessel while said proximal region extends outside of the vessel to permit control of said catheter;

an ultrasound transducer adapted to operate within said elongate sheath, and capable of rotation, and simultaneous longitudinal translation relative to said sheath along a pull-back trajectory to obtain a stack of images during pull-back; and a drive shaft operably connected to the ultrasound transducer, the drive shaft having at least four radiopaque markers disposed about its distal region, wherein said markers enable determination of the pull-back trajectory in the region of interest.

33. The catheter of claim 32, wherein said radiopaque markers are separated by equally spaced distances along the catheter longitudinal centerline.

34. The catheter of claim 32, wherein said radiopaque markers comprise thin metal rings mounted on the distal region of said drive shaft.

35. The catheter of claim 32, wherein said radiopaque markers are arranged in a helical pattern along said drive shaft.

36. The catheter of claim 32, further comprising at least one acoustical indexing marker disposed about the distal region of said sheath.

37. The catheter of claim 32, wherein said acoustical indexing marker extends longitudinally parallel to the catheter longitudinal centerline.

38. The catheter of claim 32, wherein said drive shaft is substantially more flexible than said elongate sheath.

39. The catheter of claim 32, wherein said drive shaft further includes an angiographic orientation marker which is radially fixed relative to said ultrasound transducer to permit X-ray visualization of rotational orientation of said ultrasound transducer.

40. The catheter of claim 32, wherein said transducer further includes a radiopaque component.

41. The catheter of claim 32, wherein the markers are spaced by distances of no greater than 20 millimeters as measured along the catheter longitudinal centerline.

42. The catheter of claim 32, wherein the markers are spaced by distances of no less than 0.8 millimeters as measured along the catheter longitudinal centerline.

* * * * *